United States Patent [19]

Grundei

[11] Patent Number: 5,649,928
[45] Date of Patent: Jul. 22, 1997

[54] DEVICE FOR DETERMINING RESECTION SURFACES OF FEMUR AND TIBIA IN PREPARATION FOR IMPLANTATION OF TOTAL KNEE ENDOPROSTHESIS

[75] Inventor: Hans Grundei, Lübeck, Germany

[73] Assignee: Eska Medical GmbH & Co., Lübeck, Germany

[21] Appl. No.: 498,725

[22] Filed: Jul. 5, 1995

[30] Foreign Application Priority Data

Jul. 8, 1994 [DE] Germany .................. 44 23 717.0

[51] Int. Cl.⁶ .................................................. A61B 17/58
[52] U.S. Cl. ......................... 606/88; 606/89; 606/96; 606/86
[58] Field of Search .................. 606/86, 87, 88, 606/89, 96, 97, 98, 105

[56] References Cited

U.S. PATENT DOCUMENTS

| | | | |
|---|---|---|---|
| 4,487,203 | 12/1984 | Androphy. | |
| 4,938,762 | 7/1990 | Wehrli | 606/88 |
| 5,282,803 | 2/1994 | Lackey | 606/88 |
| 5,304,181 | 4/1994 | Caspari et al. | 606/80 |
| 5,486,178 | 1/1996 | Hodge | 606/102 |
| 5,514,143 | 5/1996 | Bonutti et al. | 606/88 |

FOREIGN PATENT DOCUMENTS

| | | |
|---|---|---|
| 0 189 253 | 7/1986 | European Pat. Off. . |
| 0 243 109 A2 | 10/1987 | European Pat. Off. . |
| 0 466 659 A3 | 1/1992 | European Pat. Off. . |
| 0 474 320 A1 | 3/1992 | European Pat. Off. . |

OTHER PUBLICATIONS

Zimmer–Deloro Surgical Ltd.—Manual of Operative Technique—The Attenborough Total Knee System.

Von R. Forst and B. Hausmann, A Special Jig For Tibial Resection For The Implantation Of GSB–knee–prostheses In Problematic Cases, *med–orthop–Techn.*, pp. 162–166, 1984.

*Primary Examiner*—Michael Powell Buiz
*Assistant Examiner*—Mark S. Leonardo
*Attorney, Agent, or Firm*—Panitch Schwarze Jacobs & Nadel, P.C.

[57] ABSTRACT

A device for determining resection surfaces on the femur (20) and on tibia (10) in preparation for implantation of a total knee endoprosthesis includes a femoral saw template (12) and a removable tibial component (35) which can be locked in the area of the tibial tuberosity and repositioned there in exactly the same place. The tibial component has a fixed plate and a movable plate. The frontal plane of the tibia is first established and, using the movable plate, pushed in parallel in the direction of the femoral saw template (12), which at this stage is arranged on the frontal aspect of the femur (10) for pivoting around the femoral axis. The movable plate (24) of the tibial component (35) is pushed until finally at least a linear contact between tibia positioners (25) of the movable plate and the femoral saw template (12) is created. The device achieves precise resection surfaces on the femur (10) in such a way that the dorsal and ventral cuts in the femur (10) run exactly parallel to the frontal aspect of the tibia (20).

10 Claims, 3 Drawing Sheets

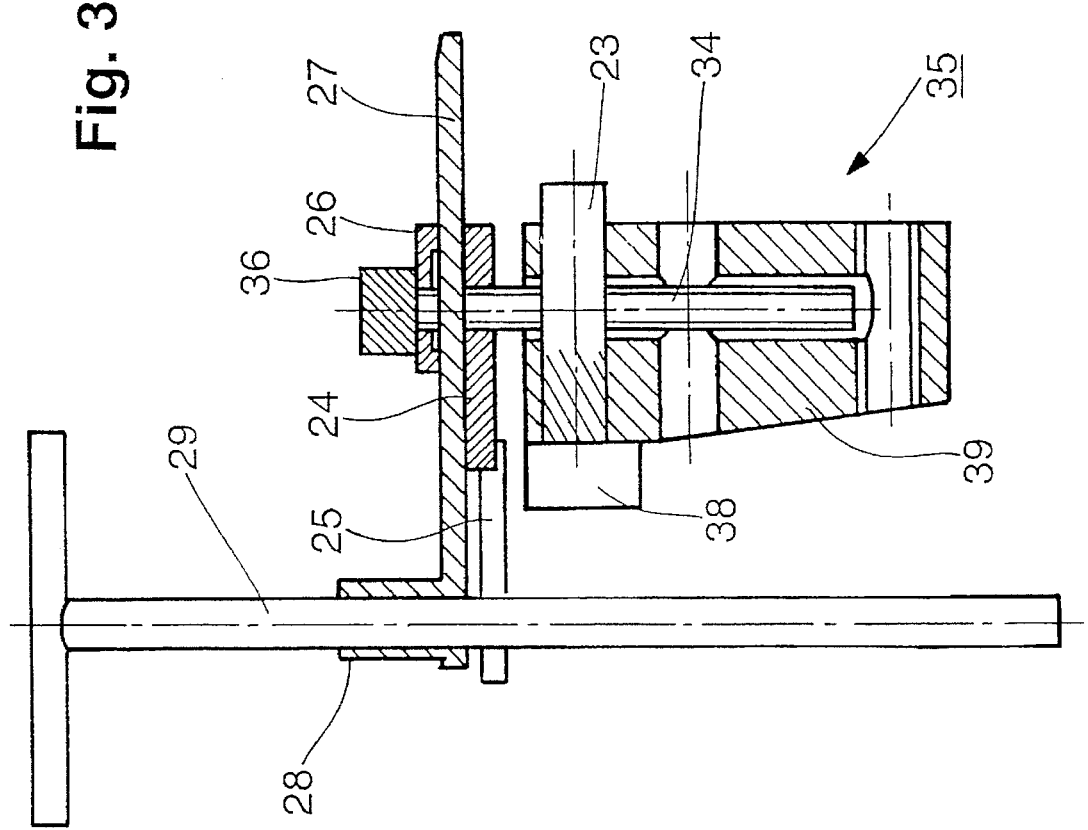
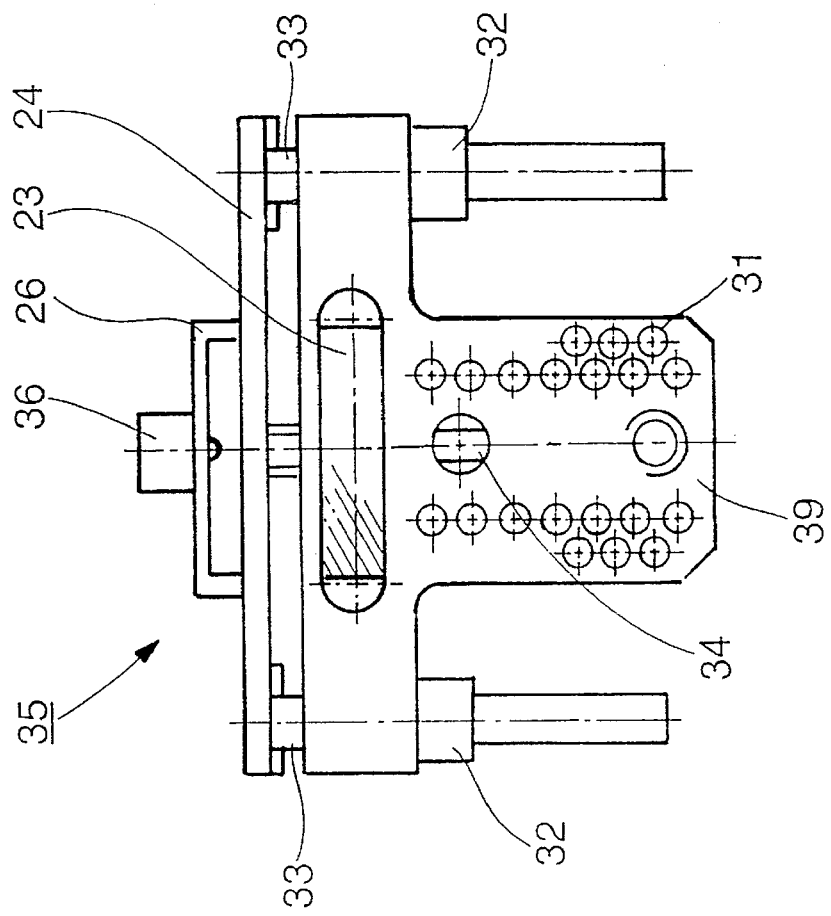

DEVICE FOR DETERMINING RESECTION SURFACES OF FEMUR AND TIBIA IN PREPARATION FOR IMPLANTATION OF TOTAL KNEE ENDOPROSTHESIS

FIELD OF THE INVENTION

The present invention concerns a device for the determination of resection surfaces of the human femur and tibia in preparation for implantation of a total knee endoprosthesis.

BACKGROUND OF THE INVENTION

Before a total knee endoprosthesis, as these are known, for example, in DE-39 22 294 C1 and DE-41 41 757 C1, can be implanted, the bordering bone regions of the femur and tibia must be resected in an appropriate manner in order to provide standard mating surfaces corresponding to the predetermined geometry of the endoprosthesis. At present, the frontal aspects of the tibia and femur are generally resected. At the very least, the femur receives an additional so-called dorsal cut as well as a ventral cut, because the femur portions of the total endoprostheses in normal use today are so constructed as to fasten into the resulting resection surfaces (dorsal, ventral and frontal) in the fashion of a clamp.

The exact location of the resection lines in this regard is extremely difficult to choose.

Until now, the orientation of the tibia to the femur with a valgus angle of from 2.5° to 7.5° was accomplished in such cases by visual inspection by an operator with some experience in such operations. The template for the saw was then attached according to this placement and the resection carried out with an oscillating bone saw.

This admittedly requires substantial experience on the part of the operator. Beginners naturally have great difficulty, as do even very experienced operators under the stressful conditions of a surgical procedure.

It can be said that both the ventral and dorsal cuts in the femur bone must be so oriented that they run parallel to the frontal resection surface of the tibia, so that the total knee endoprosthesis is properly oriented along the axis. The endoprosthesis is properly oriented if no asymmetric stress on the joint occurs, which can lead to increased wear on one portion of the gliding surface of the tibial component of the endoprosthesis through the rebuilt condyles of the femoral component of the joint.

SUMMARY OF THE INVENTION

Seen against this background, an object of the present invention is to provide a device which allows a simpler, albeit more precise, method of determining the resection surfaces of the femur and tibia in preparation for implantation of a total knee endoprosthesis, so that the ventral and dorsal cuts in the femur are each made parallel to the frontal resection surfaces of the tibia.

This object is accomplished through the device having the characteristics of the independent claim. Further advantageous developments follow from the dependent claims.

The result is a device which essentially comprises a femoral saw template and a tibial component which can be locked in place in the area of the tibial tuberosity but can be removed and then repositioned in a reproducible manner in precisely the same place.

According to the invention, it is provided that the tibial component comprises essentially two parallel plates which travel exactly parallel to each other through activation of a suitable push mechanism and a positioning block that serves for placement on the tibia in the region of the tibial tuberosity. One of the plates is fixed in place exactly perpendicular to the main axis of the positioning block and is designed for frontal installation on the tibia. The femoral saw template, on the other hand, comprises essentially a contact block that is exactly cuboid, the largest face of which is designed for frontal installation on the femur in such a way that it is pivotable around its central swiveling axis. When in place, that is during the operative procedure, the positions of the tibial component and the femoral saw template are so related to each other that a minimally linear contact between the movable plate and the tibial-facing surface of the saw template arises by the adjustment of the movable plate of the tibial component away from the fixed plate by actuation of the push mechanism and if, necessary, by carrying out a pivoting movement of the contact block around the swivel axis of the saw template.

The following is the operative procedure: First the tibial component is drawn onto one of the guidance skewers of known type which serves as a threading aid. Prior to doing so, the push mechanism is activated so that the movable plate nearly lies on the fixed plate. The tibial component is moved so far that the positioning block comes to rest on the tibia in the region of the tibial tuberosity and the movable plate contacts the frontal face of the tibia. The tibial component is locked into place in this position using fixation nails, for example, as further described below.

In this position the guidance skewer can now be removed together with the guidance element of the tibial component with which it is connected. From this point on the position of the tibial component in relation to the tibia remains undisturbed.

The femoral saw template comprises in its simplest embodiment a contact block which is exactly cuboid in shape and which contains a boring through its geometric center. Through this hole a guidance skewer can be threaded for insertion into the marrow cavity of the femur. This guidance skewer fixes the contact block of the saw template while still allowing it to swivel on its main axis. The tibial component and the femoral saw template are then displaced in such a relative position that the movable plate lifts up from the fixed plate through activation of the push mechanism of the tibial component and moves in the direction of the tibial-facing surface of the contact block of the femoral saw template. At some point the movable plate will first contact this surface. A further push will set the contact block into a slight swivel movement until the contact between this surface and the movable plate is at least linear, but is maximally planar. The latter occurs when the swivel axis of the contact block is exactly perpendicular to the axis of the tibia. This is obviously not always the case, and is also not necessary for the proper axial implementation of the resection which will be established using the device according to the invention.

The contact block is now fastened on the frontal aspect of the femur using fixation nails, and the guidance skewer is then removed from the femur marrow cavity. The contact block is equipped with saw slits through which a blade of an oscillating bone saw can be inserted and therefore produce, in the femur, the resection surfaces (ventral and dorsal) which have been determined.

The central point of the device according to the invention is that the exact angular relationship for the tibia (frontal to tibial axis) is achieved through the push motion of the movable plate and the resulting swivel motion of the contact block of the femoral saw template on the femur.

It is obvious that through the parallel displacement of the movable plate in relation to the fixed plate, which represents the frontal aspect of the tibia, and through the implementation of the swiveling motion of the femoral saw template, the axial relationships of each individual patient can be determined with a degree of precision formerly unknown, and therefore the optimal site for implantation of the endoprosthesis can be guaranteed.

The positioning block of the tibial component is preferably provided with a row of borings through which fixation nails can be inserted and driven into the tibia bone in order to lock the positioning block onto the tibia after successful alignment with the tibia axis, which can be pierced by the guidance skewer, as was previously mentioned. A minimum of two through borings are necessary in order to obtain a correct positioning. In order that the tibial component can be removed, but later replaced in the exact position on the tibia, the fixation nails are headless and can therefore more correctly be described as pins of a constant diameter.

The distal section of the movable plate of the tibial component is preferably provided with two tibial positioners. These tibial positioners function partially as feelers when the tibial component is attached to the tibia, since with these positioners toward the frontal position at or on the tibia, the plane is determined as they are pushed backwards in parallel through actuation of the push mechanism. It should be noted incidentally that, after the final resection, the possibility exists for an additional checking of the frontal plane of the tibia through the use of these tibia positioners, namely to determine if the frontal cut in the tibia has been performed in the correct plane. This is only the case if the tibial component is again locked in correct position on the tibia following preparations for implantation and both tibial positioners simultaneously contact the frontal resection surfaces of the tibia.

The previously mentioned guidance element, by means of which the tibial component is initially oriented to the axis of the tibia, can be inserted in a guidance sleeve carried on the movable plate of the tibial component, according to a preferred embodiment. The guidance element then runs from ventral to dorsal and has on its dorsal end a guidance bushing for the previously-mentioned guidance skewer which is driven into the marrow cavity of the tibia.

Alternatively or additionally to the orientation aid for the tibial component in the form of the previously-mentioned guidance skewer, an external orientation aid can be affixed to the positioning block, namely in the form of a directional rod. The operator orients this directional rod exactly with the visible axis of the tibia. The remaining steps correspond to those as further described above.

The additional advantageous features described below refer to the second component of the device, namely the femoral saw template.

It is preferred that the swivel axis for the femoral saw template be formed by a femoral guidance skewer which is inserted into the marrow cavity of the femur. Such a femoral guidance skewer is known and, can for example, be formed in a particularly preferred manner according to DE-U-93 17 230. For adjustment of the valgus angle it can incidentally be provided that the swivel axis of the femoral saw template coincides with the boring axis of one of the eccentric bushings built into the contact block. Depending upon the eccentricity of the through boring of the bushing, the valgus position (valgus angle) will be adjusted in the range between 2.5° and 7.5°.

A minimum of one slot is provided in the contact block through which a blade of an oscillating bone saw can be inserted. In this way the resection can be finally performed dorsally and ventrally on the femur.

In order to more exactly define the position of the contact block on the femur, an angle attachment is preferably provided extending from the block, a leg of the extension extending exactly perpendicular to the ventral-facing surface of the contact block in the longitudinal direction of the femur. This leg carries on its distal end a femoral contact feeler in the form of a bolt which faces the femur and is exactly perpendicular to the leg. In this embodiment the position of the saw template on the frontal aspect of the femur is exactly determined, first by the guidance skewer onto which the saw template is threaded and which is driven into the marrow cavity of the femur, and further by the just-described angle attachment, leg and femoral contact feeler, which are in an exact angular relationship to the contact block.

In the saw template, similarly as in the tibial component, there are through borings which run through it for receiving fixation nails or pins which removably lock the device in place.

Briefly, here are the important steps for use of an embodiment of the device according to the invention in chronological order:

1. Threading the tibial component onto the tibial guidance skewer (generally available);

2. Opening the marrow cavity of the tibia and driving in the guidance skewer until the tibial component, with its plates in contact with each other, comes to lie on the tibia, wherein the movable plate is preferably provided with tibial positioners;

3. Locking the tibial component in place using fixation nails;

4. Removing the tibial guidance skewer and guidance element;

5. Threading the femoral saw template onto the femoral guidance skewer;

6. Opening the marrow cavity of the femur and driving in the guidance skewer until the contact block lies against the frontal aspect of the femur;

7. Carrying out the parallel motion of the movable plate in relation to the fixed plate of the tibial component until at least a linear contact with the saw template is achieved;

8. Locking the femoral saw template in this position on the frontal aspect of the femur;

9. Removing the tibial component (not including the fixation nails);

10. Carrying out the femoral resection cuts (dorsal and ventral);

11. Removing the femoral resection aids;

12. Replacing the tibial component on the tibia;

13. Properly repositioning using the fixation nails remaining in the bone;

14. Carrying out the tibial resection cuts;

15. Checking the tibial cuts using the tibial positioners. Correct cuts are achieved if both positioners simultaneously come to rest on the resection surfaces.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 2 is a view of the tibial component as seen in the direction of the arrow II in FIG. 1;

FIG. 3 is a cross-sectional view of the tibial component with attached guidance element and guidance skewer.

In the following, like parts are indicated with like reference numerals.

DETAILED DESCRIPTION OF PREFERRED EMBODIMENT

Figure 1:
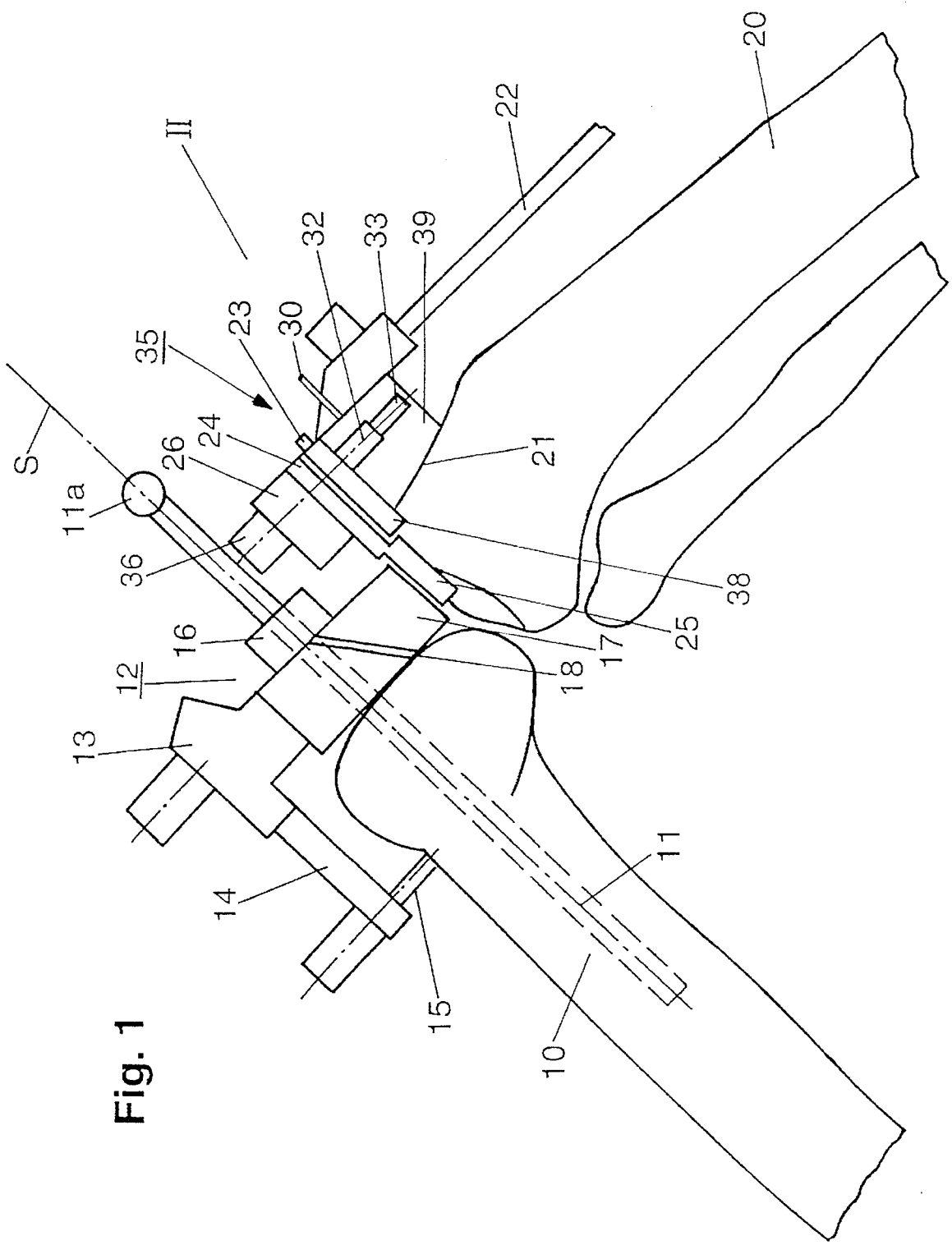
FIG. 1 shows the entire device of the invention in position relative to the femur and to the tibia.

In FIG. 1 the entire device is illustrated through an embodiment showing particularly how it is affixed to the femur 10 and to the tibia 20. The device essentially comprises the femoral saw template 12 and the tibial component 35. The function of the device according to the invention will be concisely explained with reference to FIG. 1.

The tibial component 35 lies on the tibia, namely with its positioning block 39 in the region of the tibial tuberosity 21. The alignment is produced through the external alignment aid 22 which is so positioned as to run parallel to the tibia axis. The tibial component 35 is held in place on the tibia 20 using fixation nails 30. The alignment of the tibial component 35 is accomplished in such a way that the tibial positioners 25 of the movable plate 24 rest on the frontal aspect of the tibia 20. At this stage the movable plate 24 lies on the fixed plate 38 of the tibial component 35. This is accomplished through an appropriate activation of the push mechanism which here comprises a knurled (thumb) screw head 23 and a threaded spindle 34 which runs inside the positioning block 39 (see FIGS. 2 and 3).

In this view only one of two guidance casings 32 for the guidance rods 33 can be seen. These serve to guide the movable plate 24 into a position exactly parallel to the fixed plate 38 when the push mechanism is activated.

In the side view the movable plate 24 of the tibial component 35 is seen to be connected to the guidance sleeve 26, into which a guidance element 27 (see FIG. 3) can be inserted for alignment of the tibial component 35 to the tibial axis using a guidance skewer 29 (see FIG. 3), additionally or alternatively to alignment by means of the external alignment aid 22 (FIG. 3). This guidance element 27 carries on its dorsal end a guidance bushing 28 for the tibial guidance skewer 29

The femoral saw template 12 comprises essentially the contact block 17 which lies against the frontal aspect of the femur 10.

The contact block 17, although locked on the frontal aspect of the femur 10 preferably using fixation nails, nevertheless remains pivotally mounted in the position shown around the swivel axis (S), which in the embodiment shown is formed by the guidance skewer 11 with the 'dumb-bell' 11a, which is driven into the marrow cavity of the femur 10. Provided on the contact block 17 is an eccentric bushing 16 with an eccentric boring. The eccentricity of this boring produces a valgus angle between 2.5° and 7.5°.

The contact block 17 is exactly cuboid in shape. For a more exact alignment of the femoral saw template 12 there is an angle attachment 13 which extends from the contact block 17, as illustrated. The angle attachment 13 is provided with a leg 14 which extends in the direction of the femur at 90° to the ventral aspect of the contact block 17. The leg has a femoral contact feeler 15 on its distal end, which is shown here as a bolt which is exactly perpendicular to the leg 14, pointing in the direction of the femur 10. The femoral contact feeler 15 lies on the ventral side of the femur 10.

In the position illustrated the knurled screw head 23 is now turned so that the movable plate 24 lifts off the fixed plate 38 and travels in the direction of the contact block 17. The first contact between the tibial component 35 and the saw template 12 takes place at individual points between the tibial positioners 25 and the surface of the contact block 17 which faces the tibia. As the knurled screw head 23 is turned further the contact block 17 swivels so that finally at least a linear contact between the tibial positioners 25 and the contact block 17 is created. This parallel movement of the frontal aspect of the tibia against the saw template assures that the dorsal and ventral cuts to be made in the femur will run parallel to the frontal aspect of the tibia.

The saw template 12 is provided with slits 18 (only one is shown) for the oscillating bone saw, in order to guide the blade of the saw for the exact cut. In addition, the saw template 12 is locked on the frontal aspect of the femur 10 using, for example, fixation nails (not shown) which run through borings (not shown) in the contact block 17. Thereafter, the guidance skewer 11 can be removed by pulling the 'dumb-bell' 11a. The same applies to the eccentric bushing 16, so that the operator has free access to the slits 18 and is able to create the necessary resection surfaces on the femur 10.

FIG. 2 shows the view of the tibial component 35 in the direction of arrow II in FIG. 1. The borings 31 for the fixation nails 30 are to be emphasized here. In the embodiment shown an entire row of borings 31 is provided so that it is possible to lock the device with greater certainty onto a bone that has possibly been damaged. At least two borings are absolutely necessary in order to retain the ability to reproduce the position of the tibial component 35 on the tibia 20.

FIG. 2 clearly shows the parallel guidance of the movable plate 24 in relation to the rest of the tibial component 35. This is accomplished using the guidance casings 32 and guidance rods 33 inserted into them, which are fastened from below onto the movable plate 24. The pushing movement is achieved through the rotation of the knurled screw head 23 which works together with the threaded spindle 34 within the positioning block 39.

Also clearly visible in this view is the previously-mentioned guidance sleeve 26 for the guidance element 27 (FIG. 3). The guidance sleeve 26 supports a sphere casing 36 in which a spring-powered sphere is housed in such a way that it partially extends into the guidance sleeve 26. This sphere works together with the guidance element 27 to increase the supporting power of the guidance element 27. In this way, the guidance element 27 cannot simply leave a position where it is once placed, but can only be moved in a specific way which requires a certain application of force.

As previously mentioned, the guidance element 27 is equipped on its dorsal end with a guidance bushing 28 in which the guidance skewer 29 can be inserted. In this regard, the longitudinal axis of the guidance bushing 28 lies exactly perpendicular to the leg of the guidance element 27.

Figure 4:
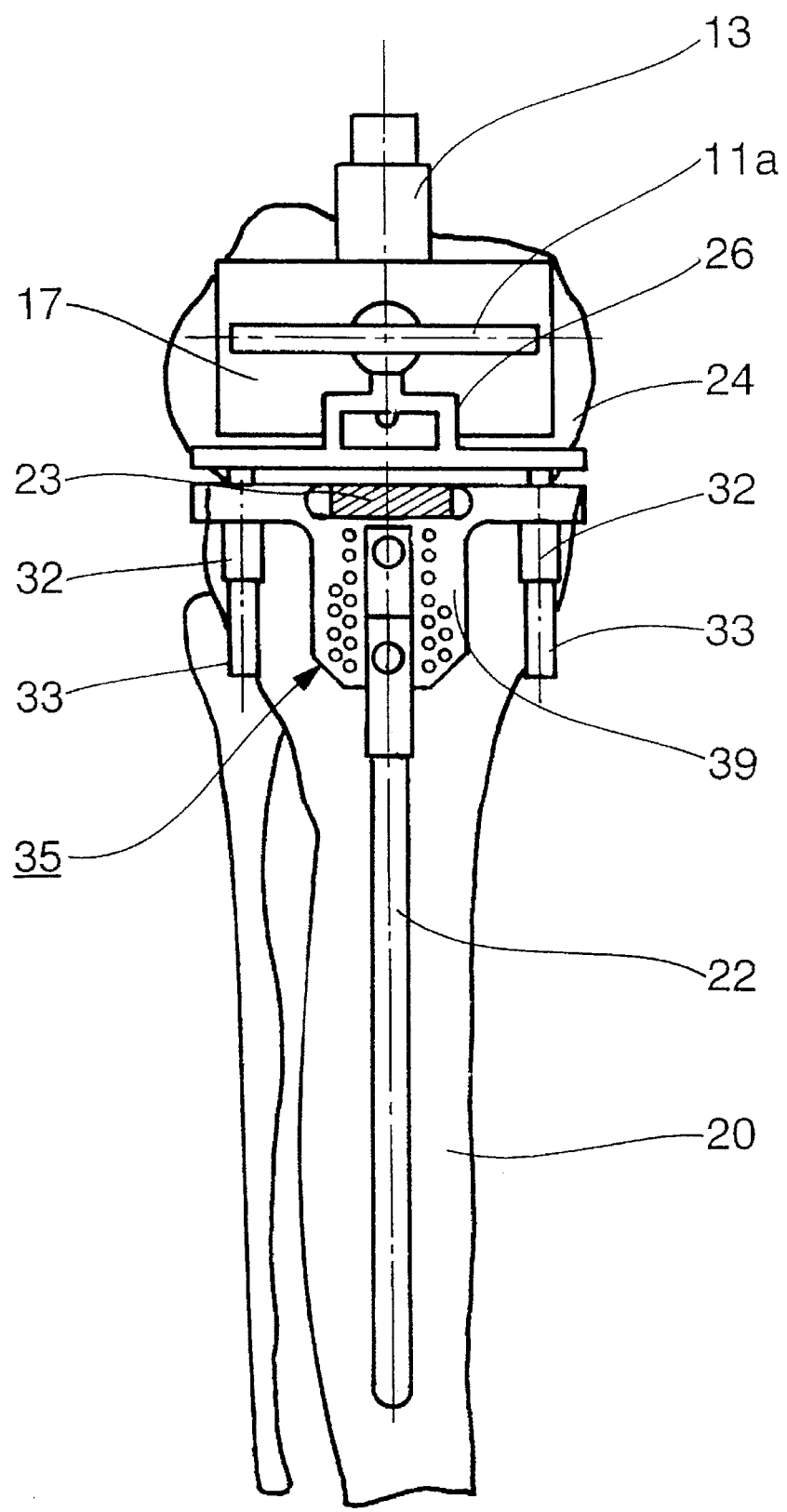
FIG. 4 is a schematic view of the tibia and femur in bent position with the device attached.

Finally, FIG. 4 exists simply to complete the total picture. All pieces have already been discussed in the previous description and clarified through use of the diagrams. FIG. 4 shows the complete device as seen ventrally. Worthy of mention here remains only the alignment aid 22 in the form of a directional rod. This is aligned by the operator with the axis of the tibia. As clearly visible, the guidance element 27 (FIG. 3) has been removed from the guidance sleeve 26 along with the guidance skewer 29, and the device is ready for the parallel push movement of the frontal tibial plate toward the femoral saw template 12.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. A device for determining resection surfaces on a femur and a tibia in preparation for implantation of a total knee endoprosthesis comprising a femoral saw template and a removable tibial component which is located in a region of tibial tuberosity and is reproducibly repositionable there in exactly the same place, wherein the tibial component (35) comprises two parallel plates (24, 38) which are movable exactly parallel relative to each other by a push mechanism (23, 34), the parallel plates are mounted on a positioning block (39) for positioning against the tibia (20), one of the plates (38) being fixed and lying exactly perpendicular to a main axis of the positioning block (39) and the other plate (24) being movable and configured to rest on a frontal aspect of the tibia (20);

the femoral saw template (12) comprises a contact block (17) that is exactly cuboid in shape having opposing major faces connected by four perpendicular side faces, one major face being configured for installation on a frontal aspect of the femur (10), and an aperture defined through the major faces of the contact block, a swivel axis (S) for movement of the saw template extends through the aperture;

the movable plate (24) of the tibial component (35) being movable away from the fixed plate (38) by the push mechanism toward a facing side face of the femoral saw template (12), and the contact block (17) being pivotable on the swivel axis (S) such that an at least linear contact is created between the moving plate (24) and the facing side face of the femoral saw template to accurately position the femoral saw template (12) with the femur prior to resection.

2. The device according to claim 1 wherein the positioning block (39) is equipped with a row of through borings (31) for receiving fixation nails (30).

3. The device according to claim 1 wherein the movable plate (24) is equipped with two tibial positioners (25).

4. The device according to claim 1 further comprising an external alignment aid (22) for the tibial component (35), said aid being affixed on an outer side of the positioning block (39) and being configured as a directional rod.

5. The device according to claim 1 wherein the contact block (17) has at least one slit (18) through which a blade of an oscillating bone saw can reach.

6. The device according to claim 1 wherein the saw template (12) is removably lockable on the frontal aspect of the femur by means of through borings in the template for receiving fixation nails.

7. The device according to claim 1 wherein the movable plate (24) is equipped with a guidance sleeve (26) in which a guidance element (27) is temporarily inserted, the guidance element having two ends, a guidance bushing (28) for receiving a guidance skewer (29) which is insertable into a marrow cavity of the tibia (20) is located on one end of the guidance element.

8. The device according to claim 1 wherein a femoral guidance skewer (1, 1a) is located in the aperture in the contact block (17) and is adapted for insertion into a marrow cavity of the femur (10), the swivel axis (S) for the femoral saw template (12) being located on an axis of the femoral guidance skewer.

9. The device according to claim 1 wherein an eccentric bushing having an axis is located in the aperture in the contact block (17), and the swivel axis (S) for the femoral saw template (12) lies along the axis of the eccentric bushing (16) in the contact block (17).

10. The device according to claim 1 wherein the contact block (17) has an angle attachment (13) extending therefrom, the attachment having a leg (14) with a fixed end attached to the angle attachment and a distal end, the leg extends perpendicular to the major faces, and is adapted to point along a longitudinal direction of the femur, the leg having on its distal end a femoral contact feeler (15) in the form of a bolt which extends perpendicular to the leg (14).

* * * * *